(12) United States Patent
Andreas et al.

(10) Patent No.: US 8,574,282 B2
(45) Date of Patent: Nov. 5, 2013

(54) APPARATUS AND METHODS FOR DELIVERY OF BRAIDED PROSTHESES

(75) Inventors: Bernard Andreas, Redwood City, CA (US); Ronald French, Santa Clara, CA (US); Mark E. Deem, Mountain View, CA (US); Hanson S. Gifford, III, Woodside, CA (US); Allan Will, Atherton, CA (US)

(73) Assignee: J.W. Medical Systems Ltd., Weihai Shangdong (CN)

( * ) Notice: Subject to any disclaimer, the term of this patent is extended or adjusted under 35 U.S.C. 154(b) by 115 days.

(21) Appl. No.: 13/078,749

(22) Filed: Apr. 1, 2011

(65) Prior Publication Data
US 2011/0178589 A1    Jul. 21, 2011

Related U.S. Application Data

(63) Continuation of application No. 12/040,598, filed on Feb. 29, 2008, now Pat. No. 7,938,852, which is a continuation of application No. 10/966,806, filed on Oct. 14, 2004, now Pat. No. 7,357,812, which is a continuation of application No. 10/306,620, filed on Nov. 27, 2002, now Pat. No. 7,147,656.

(60) Provisional application No. 60/336,607, filed on Dec. 3, 2001.

(51) Int. Cl.
    *A61F 2/06*    (2013.01)
(52) U.S. Cl.
    USPC ........................................................ 623/1.11
(58) Field of Classification Search
    USPC .................................. 623/1.11–1.16; 606/108
    See application file for complete search history.

(56) References Cited

U.S. PATENT DOCUMENTS

| | | |
|---|---|---|
| 4,069,825 A | 1/1978 | Akiyama |
| 4,468,224 A | 8/1984 | Enzmann et al. |
| 4,512,338 A | 4/1985 | Balko |
| 4,564,014 A | 1/1986 | Fogarty et al. |
| 4,580,568 A | 4/1986 | Gianturco |
| 4,681,110 A | 7/1987 | Wiktor |

(Continued)

FOREIGN PATENT DOCUMENTS

| | | |
|---|---|---|
| DE | 1 953 1659 | 3/1997 |
| DE | 1 963 0469 | 1/1998 |

(Continued)

OTHER PUBLICATIONS

Chu et al., "Preparation of Thermo-Responsive Core-Shell Microcapsules with a Porous Membrane and Poly(N-isopropylacrylamide) Gates," J Membrane Sci, Oct. 15, 2001; 192(1-2):27-39.

(Continued)

*Primary Examiner* — Suzette J Gherbi
(74) *Attorney, Agent, or Firm* — Kilpatrick Townsend & Stockton LLP

(57) ABSTRACT

Blood vessels and other body lumens are expanded using an evertible braided prosthesis. The braided prosthesis is delivered to the blood vessel in a radially collapsed configuration. A leading edge of the braided prosthesis is then everted so that it expands as it is advanced through the blood vessel. Optionally, the prosthesis can be provided with a biologically active substance in order to inhibit hyperplasia or have other desired biological effects.

8 Claims, 2 Drawing Sheets

(56) References Cited

U.S. PATENT DOCUMENTS

| | | | |
|---|---|---|---|
| 4,690,684 | A | 9/1987 | McGreevy et al. |
| 4,733,665 | A | 3/1988 | Palmaz |
| 4,739,762 | A | 4/1988 | Palmaz |
| 4,748,982 | A | 6/1988 | Horzewski et al. |
| 4,762,129 | A | 8/1988 | Bonzel |
| 4,770,176 | A | 9/1988 | McGreevy et al. |
| 4,775,337 | A | 10/1988 | Van Wagener et al. |
| 4,776,337 | A | 10/1988 | Palmaz |
| 4,886,062 | A | 12/1989 | Wiktor |
| 4,891,225 | A | 1/1990 | Langer et al. |
| 4,950,227 | A | 8/1990 | Savin et al. |
| 4,988,356 | A | 1/1991 | Crittenden et al. |
| 4,994,066 | A | 2/1991 | Voss |
| 4,994,069 | A | 2/1991 | Ritchart et al. |
| 4,994,298 | A | 2/1991 | Yasuda |
| 5,013,318 | A | 5/1991 | Spranza, III |
| 5,035,706 | A | 7/1991 | Giantureo et al. |
| 5,040,548 | A | 8/1991 | Yock |
| 5,061,273 | A | 10/1991 | Yock |
| 5,064,435 | A | 11/1991 | Porter |
| 5,092,877 | A | 3/1992 | Pinchuk |
| 5,102,417 | A | 4/1992 | Palmaz |
| 5,104,404 | A | 4/1992 | Wolff |
| 5,122,154 | A | 6/1992 | Rhodes |
| 5,135,535 | A | 8/1992 | Kramer |
| 5,158,548 | A | 10/1992 | Lau et al. |
| 5,192,297 | A | 3/1993 | Hull |
| 5,195,984 | A | 3/1993 | Schatz |
| 5,201,757 | A | 4/1993 | Heyn et al. |
| 5,217,495 | A | 6/1993 | Kaplan et al. |
| 5,219,355 | A | 6/1993 | Parodi et al. |
| 5,226,913 | A | 7/1993 | Pinchuk |
| 5,246,421 | A | 9/1993 | Saab |
| 5,273,536 | A | 12/1993 | Savas |
| 5,282,824 | A | 2/1994 | Gianturco |
| 5,300,085 | A | 4/1994 | Yock |
| 5,312,415 | A | 5/1994 | Palermo |
| 5,328,469 | A * | 7/1994 | Coletti .................... 604/103.09 |
| 5,334,187 | A | 8/1994 | Fischell et al. |
| 5,391,172 | A | 2/1995 | Williams et al. |
| 5,421,955 | A | 6/1995 | Lau et al. |
| 5,443,498 | A | 8/1995 | Fontaine |
| 5,445,646 | A | 8/1995 | Euteneuer et al. |
| 5,456,713 | A | 10/1995 | Chuter |
| 5,458,615 | A | 10/1995 | Klemm et al. |
| 5,470,315 | A | 11/1995 | Adams |
| 5,478,349 | A | 12/1995 | Nicholas |
| 5,484,444 | A | 1/1996 | Braunschweiler et al. |
| 5,490,837 | A | 2/1996 | Blaeser et al. |
| 5,496,346 | A | 3/1996 | Horzewski et al. |
| 5,501,227 | A | 3/1996 | Yock |
| 5,507,768 | A | 4/1996 | Lau et al. |
| 5,507,771 | A | 4/1996 | Gianturco |
| 5,514,093 | A | 5/1996 | Ellis et al. |
| 5,514,154 | A | 5/1996 | Lau et al. |
| 5,522,882 | A | 6/1996 | Gaterud et al. |
| 5,527,354 | A | 6/1996 | Fontaine et al. |
| 5,531,735 | A | 7/1996 | Thompson |
| 5,533,968 | A | 7/1996 | Muni et al. |
| 5,534,007 | A | 7/1996 | St. Germain et al. |
| 5,545,209 | A | 8/1996 | Roberts et al. |
| 5,549,551 | A | 8/1996 | Peacock, III et al. |
| 5,549,563 | A | 8/1996 | Kronner |
| 5,549,635 | A | 8/1996 | Solar |
| 5,554,181 | A | 9/1996 | Das |
| 5,562,725 | A | 10/1996 | Schmitt et al. |
| 5,571,086 | A | 11/1996 | Kaplan et al. |
| 5,591,195 | A | 1/1997 | Taheri et al. |
| 5,593,412 | A | 1/1997 | Martinez et al. |
| 5,607,444 | A | 3/1997 | Lam |
| 5,607,463 | A | 3/1997 | Schwartz et al. |
| 5,628,755 | A | 5/1997 | Heller et al. |
| 5,628,775 | A | 5/1997 | Jackson et al. |
| 5,634,928 | A | 6/1997 | Fischell et al. |
| 5,639,274 | A | 6/1997 | Fischell et al. |
| 5,662,675 | A | 9/1997 | Polanskyj Stockert et al. |
| 5,662,703 | A * | 9/1997 | Yurek et al. .................. 623/1.12 |
| 5,670,161 | A | 9/1997 | Healy et al. |
| 5,676,654 | A | 10/1997 | Ellis et al. |
| 5,683,451 | A | 11/1997 | Lenker et al. |
| 5,690,644 | A | 11/1997 | Yurek et al. |
| 5,693,085 | A | 12/1997 | Buirge et al. |
| 5,697,948 | A | 12/1997 | Marin et al. |
| 5,697,971 | A | 12/1997 | Fischell et al. |
| 5,702,418 | A | 12/1997 | Ravenscroft |
| 5,702,419 | A * | 12/1997 | Berry et al. .................. 623/1.13 |
| 5,709,701 | A | 1/1998 | Parodi |
| 5,716,393 | A | 2/1998 | Lindenberg et al. |
| 5,722,669 | A | 3/1998 | Shimizu et al. |
| 5,723,003 | A | 3/1998 | Winston et al. |
| 5,735,869 | A | 4/1998 | Fernandez-Aceytuno |
| 5,741,323 | A | 4/1998 | Pathak et al. |
| 5,749,848 | A | 5/1998 | Jang et al. |
| 5,749,890 | A | 5/1998 | Shaknovich |
| 5,749,921 | A | 5/1998 | Lenker et al. |
| 5,755,772 | A | 5/1998 | Evans et al. |
| 5,755,776 | A | 5/1998 | Al-Saadon |
| 5,755,781 | A | 5/1998 | Jayaraman |
| 5,769,882 | A | 6/1998 | Fogarty et al. |
| 5,772,669 | A | 6/1998 | Vrba |
| 5,776,141 | A | 7/1998 | Klein et al. |
| 5,792,144 | A | 8/1998 | Fischell et al. |
| 5,797,951 | A | 8/1998 | Mueller et al. |
| 5,800,519 | A | 9/1998 | Sandock |
| 5,807,398 | A | 9/1998 | Shaknovich |
| 5,824,040 | A | 10/1998 | Cox et al. |
| 5,824,041 | A | 10/1998 | Lenker et al. |
| 5,833,694 | A | 11/1998 | Poncet |
| 5,836,964 | A | 11/1998 | Richter et al. |
| 5,843,092 | A | 12/1998 | Heller et al. |
| 5,855,563 | A | 1/1999 | Kaplan et al. |
| 5,858,556 | A | 1/1999 | Eckert et al. |
| 5,870,381 | A | 2/1999 | Kawasaki et al. |
| 5,879,370 | A | 3/1999 | Fischell et al. |
| 5,891,190 | A | 4/1999 | Boneau |
| 5,895,398 | A | 4/1999 | Wensel et al. |
| 5,899,935 | A | 5/1999 | Ding |
| 5,902,332 | A | 5/1999 | Schatz |
| 5,919,175 | A | 7/1999 | Sirhan |
| 5,921,971 | A | 7/1999 | Agro et al. |
| 5,922,020 | A | 7/1999 | Klein et al. |
| 5,941,869 | A | 8/1999 | Patterson et al. |
| 5,951,585 | A | 9/1999 | Cathcart et al. |
| 5,961,536 | A | 10/1999 | Mickley et al. |
| 5,968,069 | A | 10/1999 | Dusbabek et al. |
| 5,972,027 | A | 10/1999 | Johnson |
| 5,976,107 | A | 11/1999 | Mertens et al. |
| 5,976,155 | A | 11/1999 | Foreman et al. |
| 5,980,484 | A | 11/1999 | Ressemann et al. |
| 5,980,486 | A | 11/1999 | Enger |
| 5,980,514 | A | 11/1999 | Kupiecki et al. |
| 5,980,552 | A | 11/1999 | Pinchasik et al. |
| 5,984,957 | A | 11/1999 | Laptewicz, Jr. et al. |
| 5,989,280 | A | 11/1999 | Euteneuer et al. |
| 5,993,484 | A | 11/1999 | Shmulewitz |
| 5,997,563 | A | 12/1999 | Kretzers et al. |
| 6,004,328 | A | 12/1999 | Solar |
| 6,007,517 | A | 12/1999 | Anderson |
| 6,010,530 | A | 1/2000 | Goicoechea |
| 6,022,359 | A | 2/2000 | Frantzen |
| 6,022,374 | A | 2/2000 | Imran |
| 6,027,519 | A | 2/2000 | Stanford |
| 6,033,434 | A | 3/2000 | Borghi |
| 6,036,725 | A | 3/2000 | Avellanet |
| 6,039,721 | A | 3/2000 | Johnson et al. |
| 6,042,589 | A | 3/2000 | Marianne |
| 6,056,722 | A | 5/2000 | Jayaraman |
| 6,063,111 | A | 5/2000 | Hieshima et al. |
| 6,066,155 | A | 5/2000 | Amann et al. |
| 6,068,655 | A | 5/2000 | Seguin et al. |
| 6,070,589 | A | 6/2000 | Keith et al. |
| 6,090,063 | A | 7/2000 | Makower et al. |
| 6,090,136 | A | 7/2000 | McDonald et al. |
| 6,102,942 | A | 8/2000 | Ahari |

(56) References Cited

U.S. PATENT DOCUMENTS

| | | |
|---|---|---|
| 6,106,530 A | 8/2000 | Harada |
| RE36,857 E | 9/2000 | Euteneuer et al. |
| 6,120,522 A | 9/2000 | Vrba et al. |
| 6,123,712 A | 9/2000 | Di Caprio et al. |
| 6,123,723 A | 9/2000 | Konya et al. |
| 6,126,685 A | 10/2000 | Lenker et al. |
| 6,129,756 A | 10/2000 | Kugler |
| 6,132,460 A | 10/2000 | Thompson |
| 6,139,572 A | 10/2000 | Campbell et al. |
| 6,143,016 A | 11/2000 | Bleam et al. |
| 6,165,167 A | 12/2000 | Delaloye |
| 6,165,210 A | 12/2000 | Lau et al. |
| 6,171,334 B1 | 1/2001 | Cox |
| 6,179,878 B1 | 1/2001 | Duering |
| 6,183,509 B1 | 2/2001 | Dibie |
| 6,187,034 B1 | 2/2001 | Frantzen |
| 6,190,402 B1 | 2/2001 | Horton et al. |
| 6,196,995 B1 | 3/2001 | Fagan |
| 6,200,337 B1 | 3/2001 | Moriuchi et al. |
| 6,217,585 B1 | 4/2001 | Houser et al. |
| 6,238,991 B1 | 5/2001 | Suzuki |
| 6,241,691 B1 | 6/2001 | Ferrera et al. |
| 6,241,758 B1 | 6/2001 | Cox |
| 6,248,122 B1 | 6/2001 | Klumb et al. |
| 6,251,132 B1 | 6/2001 | Ravenscroft et al. |
| 6,251,134 B1 | 6/2001 | Alt et al. |
| 6,254,612 B1 | 7/2001 | Hieshima |
| 6,254,628 B1 | 7/2001 | Wallace et al. |
| 6,258,117 B1 | 7/2001 | Camrud et al. |
| 6,264,688 B1 | 7/2001 | Herklotz et al. |
| 6,267,783 B1 | 7/2001 | Letendre et al. |
| 6,270,524 B1 | 8/2001 | Kim |
| 6,273,895 B1 | 8/2001 | Pinchuk et al. |
| 6,273,911 B1 | 8/2001 | Cox et al. |
| 6,273,913 B1 | 8/2001 | Wright et al. |
| 6,287,291 B1 | 9/2001 | Bigus et al. |
| 6,312,458 B1 | 11/2001 | Golds |
| 6,315,794 B1 | 11/2001 | Richter |
| 6,319,277 B1 | 11/2001 | Rudnick et al. |
| 6,322,586 B1 | 11/2001 | Monroe et al. |
| 6,325,823 B1 | 12/2001 | Horzewski et al. |
| 6,334,871 B1 | 1/2002 | Dor et al. |
| 6,340,366 B2 | 1/2002 | Wijay |
| 6,344,272 B1 | 2/2002 | Oldenburg et al. |
| 6,348,065 B1 | 2/2002 | Brown et al. |
| 6,350,252 B2 | 2/2002 | Ray et al. |
| 6,350,277 B1 | 2/2002 | Kocur |
| 6,357,104 B1 | 3/2002 | Myers |
| 6,361,558 B1 | 3/2002 | Hieshima et al. |
| 6,375,676 B1 | 4/2002 | Cox |
| 6,379,365 B1 | 4/2002 | Diaz |
| 6,383,171 B1 | 5/2002 | Gifford et al. |
| 6,394,995 B1 | 5/2002 | Solar et al. |
| 6,409,753 B1 | 6/2002 | Brown et al. |
| 6,415,696 B1 | 7/2002 | Erickeson et al. |
| 6,416,543 B1 | 7/2002 | Hilaire et al. |
| 6,419,693 B1 | 7/2002 | Fariabi |
| 6,425,898 B1 | 7/2002 | Wilson et al. |
| 6,428,811 B1 | 8/2002 | West et al. |
| 6,451,025 B1 | 9/2002 | Jervis |
| 6,451,050 B1 | 9/2002 | Rudakov et al. |
| 6,464,720 B2 | 10/2002 | Boatman et al. |
| 6,468,298 B1 | 10/2002 | Pelton |
| 6,468,299 B2 | 10/2002 | Stack et al. |
| 6,485,510 B1 | 11/2002 | Camrud et al. |
| 6,488,694 B1 | 12/2002 | Lau et al. |
| 6,488,702 B1 | 12/2002 | Besselink |
| 6,511,468 B1 | 1/2003 | Cragg et al. |
| 6,520,986 B2 | 2/2003 | Martin et al. |
| 6,520,987 B1 | 2/2003 | Plante |
| 6,527,789 B1 | 3/2003 | Lau et al. |
| 6,527,799 B2 | 3/2003 | Shanley |
| 6,530,944 B2 | 3/2003 | West et al. |
| 6,540,777 B2 | 4/2003 | Stenzel |
| 6,551,350 B1 | 4/2003 | Thornton et al. |
| 6,555,157 B1 | 4/2003 | Hossainy |
| 6,558,415 B2 | 5/2003 | Thompson |
| 6,562,067 B2 | 5/2003 | Mathis |
| 6,569,180 B1 | 5/2003 | Sirhan et al. |
| 6,575,993 B1 | 6/2003 | Yock |
| 6,579,305 B1 | 6/2003 | Lashinski |
| 6,579,309 B1 | 6/2003 | Loos et al. |
| 6,582,394 B1 | 6/2003 | Reiss et al. |
| 6,582,460 B1 | 6/2003 | Cryer |
| 6,585,756 B1 | 7/2003 | Strecker |
| 6,589,273 B1 | 7/2003 | McDermott |
| 6,592,549 B2 | 7/2003 | Gerdts et al. |
| 6,599,296 B1 | 7/2003 | Gillick et al. |
| 6,599,314 B2 | 7/2003 | Mathis |
| 6,602,226 B1 | 8/2003 | Smith et al. |
| 6,602,282 B1 | 8/2003 | Yan |
| 6,605,062 B1 | 8/2003 | Hurley et al. |
| 6,605,109 B2 | 8/2003 | Fiedler |
| 6,607,553 B1 | 8/2003 | Healy et al. |
| 6,613,074 B1 | 9/2003 | Mitelberg et al. |
| 6,629,992 B2 | 10/2003 | Bigus et al. |
| 6,645,517 B2 | 11/2003 | West |
| 6,645,547 B1 | 11/2003 | Shekalim et al. |
| 6,656,212 B2 | 12/2003 | Ravenscroft et al. |
| 6,660,031 B2 | 12/2003 | Tran et al. |
| 6,660,381 B2 | 12/2003 | Halas et al. |
| 6,663,660 B2 | 12/2003 | Dusbabek et al. |
| 6,666,883 B1 | 12/2003 | Seguin et al. |
| 6,676,693 B1 | 1/2004 | Belding et al. |
| 6,676,695 B2 | 1/2004 | Solem |
| 6,679,909 B2 | 1/2004 | McIntosh et al. |
| 6,685,730 B2 | 2/2004 | West et al. |
| 6,692,465 B2 | 2/2004 | Kramer |
| 6,699,280 B2 | 3/2004 | Camrud et al. |
| 6,699,281 B2 | 3/2004 | Vallana et al. |
| 6,699,724 B1 | 3/2004 | West et al. |
| 6,702,843 B1 | 3/2004 | Brown |
| 6,709,379 B1 | 3/2004 | Brandau et al. |
| 6,709,440 B2 | 3/2004 | Callol et al. |
| 6,712,827 B2 | 3/2004 | Ellis et al. |
| 6,712,845 B2 | 3/2004 | Hossainy |
| 6,723,071 B2 | 4/2004 | Gerdts et al. |
| 6,736,842 B2 | 5/2004 | Healy et al. |
| 6,743,219 B1 | 6/2004 | Dwyer et al. |
| 6,743,251 B1 | 6/2004 | Eder |
| 6,761,734 B2 | 7/2004 | Suhr |
| 6,776,771 B2 | 8/2004 | van Moorlegem et al. |
| 6,778,316 B2 | 8/2004 | Halas et al. |
| 6,790,227 B2 | 9/2004 | Burgermeister |
| 6,800,065 B2 | 10/2004 | Duane et al. |
| 6,825,203 B2 | 11/2004 | Pasternak et al. |
| 6,837,901 B2 | 1/2005 | Rabkin et al. |
| 6,849,084 B2 | 2/2005 | Rabkin et al. |
| 6,852,252 B2 | 2/2005 | Halas et al. |
| 6,855,125 B2 | 2/2005 | Shanley |
| 6,858,034 B1 | 2/2005 | Hijlkema et al. |
| 6,878,161 B2 | 4/2005 | Lenker |
| 6,884,257 B1 | 4/2005 | Cox |
| 6,893,417 B2 | 5/2005 | Gribbons et al. |
| 6,896,695 B2 | 5/2005 | Mueller et al. |
| 6,899,728 B1 * | 5/2005 | Phillips et al. ............... 623/1.13 |
| 6,913,619 B2 | 7/2005 | Brown et al. |
| 6,918,928 B2 | 7/2005 | Wolinsky et al. |
| 6,939,376 B2 | 9/2005 | Shulz et al. |
| 6,945,989 B1 | 9/2005 | Betelia et al. |
| 6,945,995 B2 | 9/2005 | Nicholas |
| 6,951,053 B2 | 10/2005 | Padilla et al. |
| 6,962,603 B1 | 11/2005 | Brown et al. |
| 6,964,676 B1 | 11/2005 | Gerberding et al. |
| 6,991,646 B2 | 1/2006 | Clerc et al. |
| 6,994,721 B2 | 2/2006 | Israel |
| 7,005,454 B2 | 2/2006 | Brocchini et al. |
| 7,022,132 B2 | 4/2006 | Kocur |
| 7,029,493 B2 | 4/2006 | Majercak et al. |
| 7,037,327 B2 | 5/2006 | Salmon et al. |
| 7,090,694 B1 | 8/2006 | Morris et al. |
| 7,101,840 B2 | 9/2006 | Brocchini et al. |
| 7,131,993 B2 | 11/2006 | Gregorich |
| 7,137,993 B2 | 11/2006 | Acosta et al. |

(56) References Cited

U.S. PATENT DOCUMENTS

| | | |
|---|---|---|
| 7,141,063 B2 | 11/2006 | White et al. |
| 7,147,655 B2 | 12/2006 | Chermoni |
| 7,147,656 B2 * | 12/2006 | Andreas et al. ............ 623/1.11 |
| 7,169,172 B2 | 1/2007 | Levine et al. |
| 7,169,174 B2 | 1/2007 | Fischell et al. |
| 7,172,620 B2 | 2/2007 | Gilson |
| 7,175,654 B2 | 2/2007 | Bonsignore et al. |
| 7,182,779 B2 | 2/2007 | Acosta et al. |
| 7,192,440 B2 | 3/2007 | Andreas et al. |
| 7,208,001 B2 | 4/2007 | Coyle et al. |
| 7,208,002 B2 | 4/2007 | Shelso |
| 7,220,275 B2 | 5/2007 | Davidson et al. |
| 7,220,755 B2 | 5/2007 | Betts et al. |
| 7,223,283 B2 | 5/2007 | Chouinard |
| 7,238,197 B2 | 7/2007 | Sequin et al. |
| 7,241,308 B2 | 7/2007 | Andreas et al. |
| 7,244,336 B2 | 7/2007 | Fischer et al. |
| 7,270,668 B2 | 9/2007 | Andreas et al. |
| 7,294,146 B2 | 11/2007 | Chew et al. |
| 7,300,456 B2 | 11/2007 | Andreas et al. |
| 7,309,350 B2 | 12/2007 | Landreville et al. |
| 7,314,480 B2 | 1/2008 | Eidenschink et al. |
| 7,320,702 B2 | 1/2008 | Hammersmark et al. |
| 7,323,006 B2 | 1/2008 | Andreas et al. |
| 7,326,236 B2 | 2/2008 | Andreas et al. |
| 7,351,255 B2 | 4/2008 | Andreas |
| 7,534,449 B2 | 5/2009 | Saltzman et al. |
| 7,699,886 B2 | 4/2010 | Sugimoto |
| 7,918,881 B2 | 4/2011 | Andreas et al. |
| 7,993,388 B2 | 8/2011 | Lee et al. |
| 8,257,427 B2 | 9/2012 | Andersen et al. |
| 8,317,850 B2 * | 11/2012 | Kusleika ................ 623/1.12 |
| 2001/0020154 A1 | 9/2001 | Bigus et al. |
| 2001/0020173 A1 | 9/2001 | Klumb et al. |
| 2001/0020181 A1 | 9/2001 | Layne |
| 2001/0035902 A1 | 11/2001 | Iddan et al. |
| 2001/0044595 A1 | 11/2001 | Reydel et al. |
| 2001/0044632 A1 | 11/2001 | Daniel et al. |
| 2001/0049547 A1 | 12/2001 | Moore |
| 2002/0007212 A1 | 1/2002 | Brown et al. |
| 2002/0037358 A1 | 3/2002 | Barry et al. |
| 2002/0045914 A1 * | 4/2002 | Roberts et al. ............ 606/192 |
| 2002/0052642 A1 | 5/2002 | Cox et al. |
| 2002/0087186 A1 | 7/2002 | Shelso |
| 2002/0091439 A1 | 7/2002 | Baker et al. |
| 2002/0092536 A1 | 7/2002 | LaFontaine et al. |
| 2002/0107560 A1 | 8/2002 | Richter |
| 2002/0111671 A1 | 8/2002 | Stenzel |
| 2002/0123786 A1 | 9/2002 | Gittings et al. |
| 2002/0128706 A1 | 9/2002 | Ospyka |
| 2002/0138132 A1 | 9/2002 | Brown |
| 2002/0151924 A1 | 10/2002 | Shiber |
| 2002/0151955 A1 | 10/2002 | Tran et al. |
| 2002/0156496 A1 | 10/2002 | Chermoni |
| 2002/0165599 A1 | 11/2002 | Nasralla |
| 2002/0168317 A1 | 11/2002 | Daighighian et al. |
| 2002/0177890 A1 | 11/2002 | Lenker |
| 2002/0183763 A1 | 12/2002 | Callol et al. |
| 2002/0188343 A1 | 12/2002 | Mathis |
| 2002/0188347 A1 | 12/2002 | Mathis |
| 2002/0193873 A1 | 12/2002 | Brucker et al. |
| 2003/0045923 A1 | 3/2003 | Bashiri et al. |
| 2003/0093143 A1 | 5/2003 | Zhao et al. |
| 2003/0097169 A1 | 5/2003 | Brucker et al. |
| 2003/0114912 A1 | 6/2003 | Sequin et al. |
| 2003/0114919 A1 | 6/2003 | McQuiston et al. |
| 2003/0114922 A1 | 6/2003 | Iwasaka et al. |
| 2003/0125791 A1 * | 7/2003 | Sequin et al. ............ 623/1.11 |
| 2003/0125800 A1 | 7/2003 | Shulze et al. |
| 2003/0125802 A1 | 7/2003 | Callol et al. |
| 2003/0135259 A1 | 7/2003 | Simso |
| 2003/0135266 A1 | 7/2003 | Chew et al. |
| 2003/0139796 A1 | 7/2003 | Sequin et al. |
| 2003/0139797 A1 | 7/2003 | Johnson et al. |
| 2003/0139798 A1 | 7/2003 | Brown et al. |
| 2003/0163085 A1 | 8/2003 | Tanner et al. |
| 2003/0176909 A1 | 9/2003 | Kusleika |
| 2003/0191516 A1 | 10/2003 | Weldon et al. |
| 2003/0195609 A1 | 10/2003 | Berenstein |
| 2003/0199821 A1 | 10/2003 | Gerdts et al. |
| 2003/0204238 A1 | 10/2003 | Tedeschi |
| 2003/0208223 A1 | 11/2003 | Kleiner |
| 2003/0212447 A1 | 11/2003 | Euteneuer |
| 2003/0225446 A1 | 12/2003 | Hartley |
| 2004/0015224 A1 | 1/2004 | Armstrong et al. |
| 2004/0024450 A1 | 2/2004 | Shulze et al. |
| 2004/0030380 A1 | 2/2004 | Shulze et al. |
| 2004/0044395 A1 | 3/2004 | Nelson |
| 2004/0073290 A1 | 4/2004 | Chouinard |
| 2004/0088044 A1 | 5/2004 | Brown et al. |
| 2004/0093061 A1 | 5/2004 | Acosta et al. |
| 2004/0093067 A1 | 5/2004 | Israel |
| 2004/0106979 A1 | 6/2004 | Goicoechea |
| 2004/0111145 A1 | 6/2004 | Serino et al. |
| 2004/0117008 A1 | 6/2004 | Wnendt et al. |
| 2004/0143322 A1 | 7/2004 | Litvack et al. |
| 2004/0176832 A1 | 9/2004 | Hartley et al. |
| 2004/0181239 A1 | 9/2004 | Dorn et al. |
| 2004/0186551 A1 | 9/2004 | Kao et al. |
| 2004/0193245 A1 | 9/2004 | Deem et al. |
| 2004/0215165 A1 | 10/2004 | Coyle et al. |
| 2004/0215312 A1 | 10/2004 | Andreas et al. |
| 2004/0215331 A1 | 10/2004 | Chew et al. |
| 2004/0230285 A1 | 11/2004 | Gifford, III et al. |
| 2004/0243217 A1 | 12/2004 | Andersen et al. |
| 2004/0249434 A1 | 12/2004 | Andreas et al. |
| 2004/0249439 A1 | 12/2004 | Richter et al. |
| 2005/0004657 A1 | 1/2005 | Burgermeister |
| 2005/0010276 A1 | 1/2005 | Acosta et al. |
| 2005/0038494 A1 | 2/2005 | Eidenschink |
| 2005/0038505 A1 | 2/2005 | Shulze et al. |
| 2005/0049673 A1 | 3/2005 | Andreas et al. |
| 2005/0080474 A1 | 4/2005 | Andreas et al. |
| 2005/0080475 A1 | 4/2005 | Andreas et al. |
| 2005/0085897 A1 | 4/2005 | Bonsignore |
| 2005/0090846 A1 | 4/2005 | Pedersen et al. |
| 2005/0123451 A1 | 6/2005 | Nomura |
| 2005/0125051 A1 | 6/2005 | Eidenschink et al. |
| 2005/0131008 A1 | 6/2005 | Betts et al. |
| 2005/0137622 A1 | 6/2005 | Griffin |
| 2005/0143827 A1 | 6/2005 | Globerman et al. |
| 2005/0149168 A1 | 7/2005 | Gregorich |
| 2005/0165378 A1 | 7/2005 | Heinrich et al. |
| 2005/0171568 A1 | 8/2005 | Duffy |
| 2005/0182477 A1 | 8/2005 | White |
| 2005/0209674 A1 | 9/2005 | Kutscher et al. |
| 2005/0209676 A1 * | 9/2005 | Kusleika ................ 623/1.11 |
| 2005/0209680 A1 | 9/2005 | Gale et al. |
| 2005/0222671 A1 | 10/2005 | Schaeffer et al. |
| 2005/0228477 A1 | 10/2005 | Grainger et al. |
| 2005/0245637 A1 | 11/2005 | Hossainy et al. |
| 2005/0249777 A1 | 11/2005 | Michal et al. |
| 2005/0278011 A1 | 12/2005 | Peckham |
| 2005/0288764 A1 | 12/2005 | Snow et al. |
| 2005/0288766 A1 | 12/2005 | Plain et al. |
| 2006/0069424 A1 | 3/2006 | Acosta et al. |
| 2006/0173529 A1 | 8/2006 | Blank |
| 2006/0200223 A1 | 9/2006 | Andreas et al. |
| 2006/0206190 A1 | 9/2006 | Chermoni |
| 2006/0229700 A1 | 10/2006 | Acosta et al. |
| 2006/0229706 A1 | 10/2006 | Shulze et al. |
| 2006/0271150 A1 | 11/2006 | Andreas et al. |
| 2006/0271151 A1 | 11/2006 | McGarry et al. |
| 2006/0282147 A1 | 12/2006 | Andreas et al. |
| 2006/0282149 A1 | 12/2006 | Kao |
| 2006/0282150 A1 | 12/2006 | Olson et al. |
| 2006/0287726 A1 | 12/2006 | Segal et al. |
| 2007/0010869 A1 | 1/2007 | Sano |
| 2007/0027521 A1 | 2/2007 | Andreas et al. |
| 2007/0043419 A1 | 2/2007 | Nikolchev et al. |
| 2007/0067012 A1 | 3/2007 | George et al. |
| 2007/0088368 A1 | 4/2007 | Acosta et al. |
| 2007/0088420 A1 | 4/2007 | Andreas et al. |
| 2007/0088422 A1 | 4/2007 | Chew et al. |

(56) References Cited

U.S. PATENT DOCUMENTS

| | | | |
|---|---|---|---|
| 2007/0100423 A1 | 5/2007 | Acosta et al. |
| 2007/0100424 A1 | 5/2007 | Chew et al. |
| 2007/0106365 A1 | 5/2007 | Andreas et al. |
| 2007/0118202 A1 | 5/2007 | Chermoni |
| 2007/0118203 A1 | 5/2007 | Chermoni |
| 2007/0118204 A1 | 5/2007 | Chermoni |
| 2007/0129733 A1 | 6/2007 | Will et al. |
| 2007/0135906 A1 | 6/2007 | Badylak et al. |
| 2007/0156225 A1 | 7/2007 | George et al. |
| 2007/0156226 A1 | 7/2007 | Chew et al. |
| 2007/0179587 A1 | 8/2007 | Acosta et al. |
| 2007/0219612 A1 | 9/2007 | Andreas et al. |
| 2007/0219613 A1 | 9/2007 | Kao et al. |
| 2007/0265637 A1 | 11/2007 | Andreas et al. |
| 2007/0270936 A1 | 11/2007 | Andreas et al. |
| 2007/0276461 A1 | 11/2007 | Andreas et al. |
| 2007/0281117 A1 | 12/2007 | Kaplan et al. |
| 2007/0292518 A1 | 12/2007 | Ludwig |
| 2008/0004690 A1 | 1/2008 | Robaina |
| 2008/0046067 A1 | 2/2008 | Toyokawa |
| 2008/0071345 A1 | 3/2008 | Hammersmark et al. |
| 2008/0077229 A1 | 3/2008 | Andreas et al. |
| 2008/0091257 A1 | 4/2008 | Andreas et al. |
| 2008/0097299 A1 | 4/2008 | Andreas et al. |
| 2008/0097574 A1 | 4/2008 | Andreas et al. |
| 2008/0125850 A1 | 5/2008 | Andreas et al. |
| 2008/0132989 A1 | 6/2008 | Snow et al. |
| 2008/0147162 A1 | 6/2008 | Andreas et al. |
| 2008/0177369 A1 | 7/2008 | Will et al. |
| 2008/0199510 A1 | 8/2008 | Ruane et al. |
| 2008/0208311 A1 | 8/2008 | Kao et al. |
| 2008/0208318 A1 | 8/2008 | Kao et al. |
| 2008/0234795 A1 | 9/2008 | Snow et al. |
| 2008/0234798 A1 | 9/2008 | Chew et al. |
| 2008/0234799 A1 | 9/2008 | Acosta et al. |
| 2008/0243225 A1 | 10/2008 | Satasiya et al. |
| 2008/0249607 A1 | 10/2008 | Webster et al. |
| 2008/0269865 A1 | 10/2008 | Snow et al. |
| 2009/0076584 A1 | 3/2009 | Mao et al. |
| 2009/0105686 A1 | 4/2009 | Snow et al. |
| 2009/0149863 A1 | 6/2009 | Andreas et al. |
| 2009/0234428 A1 | 9/2009 | Snow et al. |
| 2009/0248137 A1 | 10/2009 | Andersen et al. |
| 2009/0248140 A1 | 10/2009 | Gerberding |
| 2009/0264979 A1 | 10/2009 | Kao et al. |
| 2009/0276030 A1* | 11/2009 | Kusleika .................. 623/1.11 |
| 2010/0004729 A1 | 1/2010 | Chew et al. |

FOREIGN PATENT DOCUMENTS

| | | |
|---|---|---|
| DE | 199 50 756 | 8/2000 |
| DE | 101 03 000 | 8/2002 |
| EP | 0 203 945 B2 | 12/1986 |
| EP | 0 274 129 B1 | 7/1988 |
| EP | 0 282 143 | 9/1988 |
| EP | 0 364 787 A1 | 4/1990 |
| EP | 0 505 686 | 9/1992 |
| EP | 0 533 960 | 3/1993 |
| EP | 0 596 145 | 5/1994 |
| EP | 0 696 447 A2 | 2/1996 |
| EP | 0 714 640 A1 | 6/1996 |
| EP | 0 797 963 A2 | 10/1997 |
| EP | 0 947 180 | 10/1999 |
| EP | 1 254 644 A1 | 11/2002 |
| EP | 1 258 230 | 11/2002 |
| EP | 1 266 638 B1 | 12/2002 |
| EP | 1 277 449 | 1/2003 |
| EP | 1 290 987 A2 | 3/2003 |
| EP | 1 318 765 A2 | 6/2003 |
| EP | 1 470 834 | 10/2004 |
| EP | 1 523 959 A2 | 4/2005 |
| EP | 1 523 960 A2 | 4/2005 |
| GB | 2277875 A | 11/1994 |
| JP | 03-133446 | 6/1991 |
| JP | 07-132148 | 5/1995 |
| JP | 10-503663 | 4/1998 |
| JP | 10-295823 | 11/1998 |
| JP | 11-503056 T | 3/1999 |
| JP | 2935561 B2 | 8/1999 |
| JP | 2001-190687 | 7/2001 |
| JP | 2002-538932 T | 11/2002 |
| JP | 2004-121343 A | 4/2004 |
| WO | 94/27667 A1 | 12/1994 |
| WO | 95/26695 A2 | 10/1995 |
| WO | 95/29647 A2 | 11/1995 |
| WO | 96/26689 | 9/1996 |
| WO | 96/33677 | 10/1996 |
| WO | 96/37167 A1 | 11/1996 |
| WO | 96/39077 A1 | 12/1996 |
| WO | 97/10778 | 3/1997 |
| WO | 97/46174 | 12/1997 |
| WO | 97/48351 | 12/1997 |
| WO | 98/20810 | 5/1998 |
| WO | 98/37833 | 9/1998 |
| WO | 98/58600 | 12/1998 |
| WO | 99/01087 A1 | 1/1999 |
| WO | 99/65421 | 12/1999 |
| WO | 00/12832 A3 | 3/2000 |
| WO | 00/15151 A1 | 3/2000 |
| WO | 00/25841 | 5/2000 |
| WO | 00/32136 | 6/2000 |
| WO | 00/41649 | 7/2000 |
| WO | 00/50116 | 8/2000 |
| WO | 00/51525 A1 | 9/2000 |
| WO | 00/56237 A2 | 9/2000 |
| WO | 00/62708 | 10/2000 |
| WO | 00/72780 | 12/2000 |
| WO | 01/26707 | 4/2001 |
| WO | 01/34063 | 5/2001 |
| WO | 01/70297 | 9/2001 |
| WO | 01/91918 A1 | 12/2001 |
| WO | 02/071975 | 9/2002 |
| WO | 02/085253 A1 | 10/2002 |
| WO | 02/098326 A1 | 12/2002 |
| WO | 03/022178 A1 | 3/2003 |
| WO | 03/021425 | 6/2003 |
| WO | 03/047651 | 6/2003 |
| WO | 03/075797 | 9/2003 |
| WO | 2004/017865 | 3/2004 |
| WO | 2004/043299 A1 | 5/2004 |
| WO | 2004/043301 | 5/2004 |
| WO | 2004/043510 | 5/2004 |
| WO | 2004/052237 A2 | 6/2004 |
| WO | 2004/087006 | 10/2004 |
| WO | 2004/091441 | 10/2004 |
| WO | 2005/009295 A1 | 2/2005 |
| WO | 2005/013853 | 2/2005 |
| WO | 2005/023153 | 3/2005 |
| WO | 2006/036939 | 4/2006 |
| WO | 2006/047520 | 5/2006 |
| WO | 2007/035805 | 3/2007 |
| WO | 2007/053187 A2 | 5/2007 |
| WO | 2007/146411 | 12/2007 |
| WO | 2008/005111 | 1/2008 |

OTHER PUBLICATIONS

Colombo, "The Invatec Bifurcation Stent Solution" Bifurcation Stents: Novel Solutions, TCT 2003, Washington: Sep. 15-19, 2003, 24 pages total.

Cooley et al., "Applications of Ink-Jet Printing Technology to BioMEMs and Microfluidic Systems," Proceedings, SPIE Conference on Microfluidics and BioMEMs, (Oct. 2001).

"Drug Delivery Stent With Holes Located on Neutral Axis" Research Disclosure, Kenneth Mason Publications, Hampshire, CB, No. 429, Jan. 2000, p. 13.

Evans Analytical Group, "Functional Sites on Non-polymeric Materials: Gas Plasma Treatment and Surface Analysis," http://www.eaglabs.com.

Joung et al., "Estrogen Release from Metallic Stent Surface for the Prevention of Restenosis," J Control Release. Sep. 19, 2003;92(1-2):83-91.

(56) References Cited

OTHER PUBLICATIONS

Lefevre et al. "Approach to Coronary Bifurcation Stenting in 2003," Euro PCR, (May 2003) 28 pages total.

"Stent". Definitions from Dictionary.com. Unabridged 9v1.01). Retrieved Sep. 22, 2006, from Dictionary.com website: <http://dictionary.reference.com/search?q=stent>.

Stimpson et al., "Parallel Production of Oligonucleotide Arrays Using Membranes and Reagent Jet Printing," BioTechniques 25:886-890 (Nov. 1998).

Tilley, "Biolimus A9-Eluting Stent Shows Promise," Medscape Medical News, Oct. 5, 2004; retrieved from the internet: <http://www.medscape.com/viewarticle/490621>, 2 pages total.

Weir et al., "Degradation of poly-L-lactide. Part 2: increased temperature accelerated degradation," Proc Inst Mech Eng H. 2004;218(5):321-30.

U.S. Appl. No. 60/336,607, filed Dec. 3, 2001, first named inventor: Bernard Andreas.

U.S. Appl. No. 60/336,767, filed Dec. 3, 2001, first named inventor: Bernard Andreas.

U.S. Appl. No. 60/336,967, filed Dec. 3, 2001, first named inventor: Sunmi Chew.

U.S. Appl. No. 60/364,389, filed Mar. 13, 2002, first named inventor: Sunmi Chew.

U.S. Appl. No. 60/440,839, filed Jan. 17, 2003, first named inventor: Bernard Andreas.

U.S. Appl. No. 60/561,041, filed Apr. 9, 2004, first named inventor: Jeffry Grainger.

U.S. Appl. No. 60/784,309, filed Mar. 20, 2006, first named inventor: Bernard Andreas.

U.S. Appl. No. 60/810,522, filed Jun. 2, 2006, first named inventor: Stephen Kaplan.

U.S. Appl. No. 60/890,703, filed Feb. 20, 2007, first named inventor: Patrick Ruane.

Supplementary European Search Report of EP Patent Application No. 07758831, dated Dec. 14, 2009.

Supplementary European Search Report of EP Patent Application No. 05744136, dated Mar. 26, 2008, 3 pages total.

Supplementary European Search Report of EP Patent Application No. 05727731.1, dated Mar. 25, 2008, 2 pages total.

\* cited by examiner

ABSTRACT AND METHODS FOR
DELIVERY OF BRAIDED PROSTHESES

CROSS-REFERENCES TO RELATED APPLICATIONS

The present application is a continuation of U.S. patent application Ser. No. 12/040,598, filed Feb. 29, 2008, which is a continuation of U.S. patent application Ser. No. 10/966,806, filed Oct. 14, 2004 (now U.S. Pat. No. 7,357,812 B2), which is a continuation of U.S. patent application Ser. No. 10/306,620, filed Nov. 27, 2002 (now U.S. Pat. No. 7,147,656), which claims priority to U.S. Provisional Patent Application Ser. No. 60/336,607, filed Dec. 3, 2001, the full disclosures of which are incorporated herein by reference.

BACKGROUND OF THE INVENTION

1. Field of the Invention.

The present invention relates generally to medical devices and methods. More particularly, the present invention relates to apparatus and methods for delivering braided and other everting prostheses within a body lumen, such as a blood vessel.

Coronary artery disease is the leading cause of death and morbidity in the United States and Western society. In particular, atherosclerosis in the coronary arteries can cause myocardial infarction, commonly referred to as a heart attack, which can be immediately fatal or even if survived, cause damage to the heart which can incapacitate the patient.

While coronary artery bypass surgery can be an effective treatment for stenosed arteries resulting from atherosclerosis or other causes, it is a highly invasive, costly procedure, which typically requires substantial hospital and recovery time. Percutaneous transluminal coronary angioplasty, commonly referred to as balloon angioplasty, is less invasive, less traumatic, and significantly less expensive than bypass surgery. Heretofore, however, balloon angioplasty has not been considered as effective a treatment as bypass surgery. The effectiveness of balloon angioplasty, however, has improved significantly with the introduction of stenting, which involves the placement of a scaffold structure within the artery which has been treated by balloon angioplasty. The stent inhibits abrupt reclosure of the artery and has some benefit in inhibiting subsequent restenosis resulting from hyperplasia.

Recently, experimental trials have demonstrated that coating stents with anti-proliferative drugs, such as paclitaxel, can significantly reduce the occurrence of hyperplasia in angioplasty treated coronary arteries which have been stented with the coated stents.

While the combination of balloon angioplasty with drug-coated stents holds great promise, significant challenges still remain. Of particular interest to the present invention, the treatment of extended or disseminated disease within an artery remains problematic. Most stents have a fixed length, typically in the range from 10 mm to 30 mm, and the placement of multiple stents to treat disease over a longer length requires the successive use of multiple balloon stent delivery catheters. Moreover, it can be difficult to stent an angioplasty-treated region of a blood vessel with the optimum stent length.

For these reasons, it would be desirable to provide improved stents, stent delivery systems, stenting methods, and the like, for the treatment of patients having coronary artery disease, as well as other occlusive diseases of the vasculature and other body lumens. In particular, it would be desirable to provide stents, delivery systems, and methods for the treatment of disseminated and variable length stenotic regions within the vasculature. For example, it would be desirable to provide a practical method which permits a physician to deliver extended lengths of braided prostheses to blood vessels and other body lumens. At least some of these objectives will be met by the inventions described hereinafter.

2. Description of the Background Art.

U.S. Pat. No. 5,755,772 describes a tubular prosthesis and method for its implantation by positioning the prosthesis at a target site, and everting an end section to lock the stent after expansion has been completed; and U.S. Pat. No. 5,769,882 describes conformable tubular prostheses and their placement in blood vessels.

BRIEF SUMMARY OF THE INVENTION

The present invention provides methods and apparatus for the stenting of body lumens, typically blood vessels, and more typically coronary arteries. The methods and systems will also find significant use in the peripheral vasculature, the cerebral vasculature, and in other ducts, such as the biliary duct, the fallopian tubes, and the like. The terms "stent" and "stenting" are defined to include any of the wide variety of expandable scaffolds which are designed to be intraluminally introduced to a treatment site and expanded in situ to apply a radially outward force against the inner wall of the body lumen at that site. Stents commonly comprise an open lattice structure, typically formed from a malleable or elastic metal.

The stents of the present invention will comprise evertible structures which radially expand upon eversion to assume a non-collapsible diameter which remains in place within the body lumen to support the luminal wall. Typically, the evertible stent structures will comprise braided structures, but other structures, such as counterwound helices, will also be capable of eversion. In some instances, laser cut helical and other patterned metal tubes, particularly those formed from nickel titanium and other shape memory alloys, may be used. Thin wall tubes formed from polymeric materials, such as polyethylene terephthalate (PET), expanded polytetrafluoroethylene (ePTFE), may also find use, even without patterning.

The braided and other evertible stent structures of the present invention may be formed from metals, including both malleable metals and elastic metals, such as shape memory metals, as well as from polymeric materials. Usually, the braided structures will comprise individual ribbons of the desired material which are interwoven to form a braid so that the braid may be axially elongated to assume a narrow diameter configuration and thereafter be everted to assume a larger diameter configuration. By "evert" it is meant that a leading edge of the prosthesis is turned outwardly and backwardly relative to the narrow diameter portion thereof. In the preferred methods and apparatus of the present invention, as described in more detail below, such eversion will be achieved by initially holding the prosthesis in its narrow diameter configuration with the leading portion everted and fixed to an outer portion of a catheter. This leading portion is referred to as the "fixed end." The remainder of the prosthesis which remains in its narrow diameter configuration is held within a passage or lumen of a delivery catheter, and means are provided for pushing the "advanceable end" of the prosthesis which is in the lumen forwardly relative to the fixed end. In this way, the leading edge of the prosthesis moves forward continuously relative to the fixed end as it everts radially outwardly.

The use of such braided and other evertible prostheses provides a number of advantages. For example, the braided structure is highly flexible, particularly in its narrow diameter configuration, allowing the introduction of relatively long stent segments without significantly limiting the ability of the delivery catheter to pass through torturous regions of the vasculature or other body lumens. Additionally, by everting the prosthesis so that its outer portion remains stationary relative to the fixed end (and thus also relative to the delivery catheter), the stent will be able to pass through relatively small body lumens since it advances much like a tractor tread in moving forwardly through the lumen. In the case of vascular treatments, the stents of the present invention will usually be used following other primary interventions, such as angioplasty, atherectomy, aneurysm repair, or the like. It will be possible, however, in certain instances, to deliver the stent without prior intervention because of the ability to advance through tight lesions and to dilate the lesion as it passes therethrough.

Usually, the methods and apparatus of the present invention will be used to deliver a single stent having a predetermined length. In other instances, however, it will be possible to provide a means for severing the stent on the catheter itself. In such cases, the methods and apparatus of the present invention will be capable of delivering variable lengths of stent depending on the nature and extent of the disease being treated. That is, the apparatus will be used to deliver the stent under fluoroscopic or other observation, and after a desired length of stent has been deployed, the deployed length can be severed from the length which remains carried within the delivery catheter.

In one aspect of the present invention, a method for delivering a prosthesis to a body lumen comprises positioning a metallic tubular prosthesis at a target site within the body lumen. The prosthesis is then everted so that an inside surface is exposed radially outwardly and advanced over a length of the wall of the body lumen. Usually, positioning comprises introducing a delivery catheter having a passage which carries the tubular prosthesis at least partly in a radially collapsed configuration. Everting usually comprises pushing the tubular prosthesis from the catheter so that a leading portion of the prosthesis everts and radially expands as it exits the catheter or passage. This is usually accomplished by forwardly advancing a portion of the catheter to push the prosthesis from the catheter. In a preferred aspect of the present invention, an advanceable segment of the prosthesis is carried in the passage in the radially collapsed configuration. A fixed end of the prosthesis is held stationary relative to the catheter in a partially everted configuration. Everting then comprises pushing a proximal end (i.e., an end or portion of the prosthesis which is radially collapsed within the delivery catheter) to cause a middle portion of the prosthesis to progressively evert and advance distally relative to the fixed end. In the case of braided prostheses, the braided structure will shorten as the radius expands so that the "advanceable" proximal end prosthesis is pushed forward at a rate which is faster than the rate at which the everted prosthesis covers the wall of the body lumen. In preferred embodiments, the prosthesis releases an active substance which inhibits hyperplasia after the prosthesis has been placed in the body lumen.

In another aspect of the present invention, a method for delivering a stent to a blood vessel comprises positioning the stent at a target site within the blood vessel and everting the stent so that an inside surface is exposed radially outwardly and advanced over a length of a wall of the blood vessel. The stent, in turn, inhibits restenosis in the blood vessel.

In another aspect of the present invention, a method for delivering a prosthesis to a body lumen involves positioning a tubular prosthesis at a target site within the body lumen, the tubular prosthesis having a total length. The tubular prosthesis is then everted so that an inside surface is exposed radially outwardly and a desired length of the tubular prosthesis is advanced over a length of a wall of the body lumen, the desired length being less than the total length. The method then includes severing a portion of the tubular prosthesis having the desired length to allow the portion to remain in the body lumen.

In another aspect of the present invention, a method for delivering a prosthesis to a body lumen involves positioning a delivery catheter carrying a tubular prosthesis at a target site within the body lumen, everting the tubular prosthesis so that an inside surface is exposed radially outwardly and advanced over a desired length of a wall of the body lumen, and deploying a portion of the tubular prosthesis having the desired length. A second length of the tubular prosthesis remains carried within the delivery catheter.

In another aspect of the present invention, an apparatus for delivering a prosthesis to a body lumen includes a catheter having a passage, a metallic tubular prosthesis carried in the passage at least partially in a radially collapsed configuration, and a slidable member in the catheter for advancing the prosthesis from the passage so that the prosthesis everts and radially expands as it is advanced. In some embodiments, the metallic tubular prosthesis is a shape memory metal. In some embodiments, the metallic tubular prosthesis comprises a braided metal structure. Alternatively, the metallic tubular prosthesis may comprise an open lattice structure.

In yet another embodiment of the present invention, an apparatus for delivering a prosthesis to a blood vessel includes a catheter having a passage, a stent carried in the passage at least partially in a radially collapsed configuration, and a slidable member in the catheter for advancing the prosthesis from the passage so that said prosthesis everts and radially expands as it is advanced. The stent is configured to inhibit restenosis in the blood vessel.

In another aspect of the invention, an apparatus for delivering a prosthesis to a body lumen includes a catheter having a passage, a tubular prosthesis carried in the passage at least partially in a radially collapsed configuration, a slidable member in the catheter for advancing the prosthesis from the passage so that said prosthesis everts and radially expands as it is advanced, and a severing member in the catheter for severing a portion of the prosthesis to allow the portion to remain in the body lumen while a second portion of the prosthesis remains carried in the catheter.

These and other aspects and embodiments of the present invention will be described in further detail below, with reference to the attached drawing figures.

DETAILED DESCRIPTION OF THE INVENTION

Figure 1:
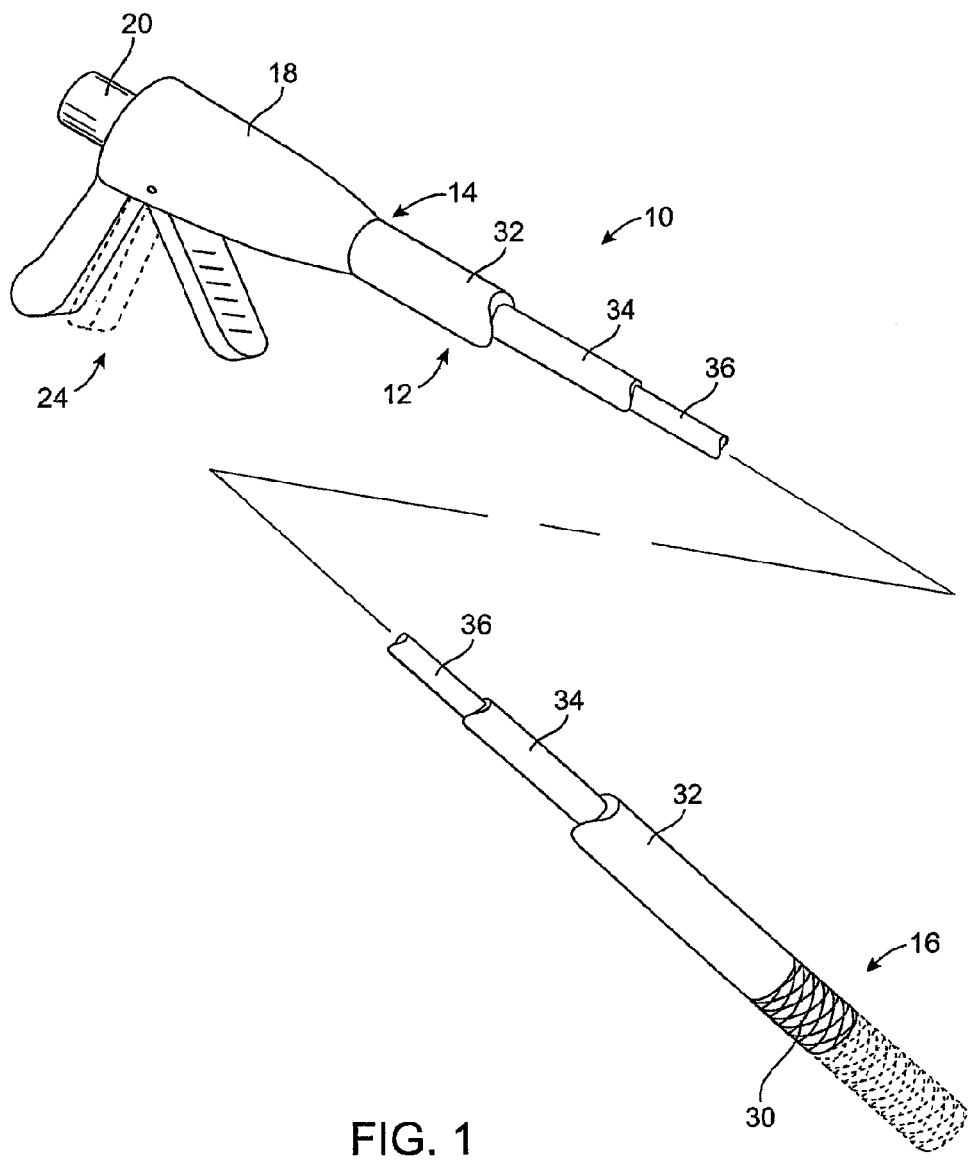
FIG. 1 is a perspective view illustrating a stent delivery catheter constructed in accordance with the principles of the present invention.

Referring now to FIG. 1, the stent delivery catheter 10 comprises a catheter body 12 having a proximal end 14 and a distal end 16. The catheter body 12 is formed from a conventional catheter material, such as a natural or synthetic polymer, such as silicone rubber, polyethylene, polyvinylchloride, polyurethane, polyester, polytetrafluoroethylene, nylon, and the like. The body may be formed as a composite having one or more reinforcement layers incorporated within a polymeric shell in order to enhance strength, flexibility, and toughness. For intravascular use, the catheter body will typically have a length in the range from 40 cm to 150 cm, usually being between 40 cm and 120 cm for peripheral blood vessels and between 110 cm and 150 cm for coronary arteries. The outer diameter of the catheter body may vary depending on the intended use, typically being between 3 French and 15 French, usually from 5 French to 9 French (one French=0.33 mm).

Catheter 10 further comprises a handle 18 at its proximal end 14. The handle has a guidewire port 20 at its distal end as well as a handle grip 24 which is actuable to extend and release evertible prosthesis 30 from the distal end 16. The catheter body 12 comprises an outer tube 32, a middle tube 34 which is coaxially and slidably mounted within a lumen of the outer tube 32, and an inner tube 36 which is slidably and coaxially mounted within a lumen of the middle tube 34. Inner tube 36 has a central lumen for receiving a guidewire, as described in detail below.

Figure 2A:
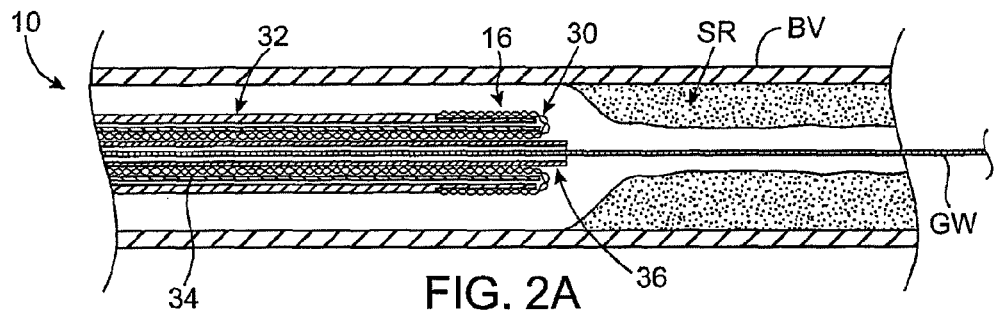
FIGS. 2A-2D illustrate use of the catheter in FIG. 1 for deploying a braided stent within a stenosed region in a blood vessel.

Referring now to FIGS. 2A-2D, delivery of the prosthesis 30 within a stenosed region SR of a blood vessel BV is described. The distal end 16 of the catheter 10 is introduced over a guidewire GW to the stenosed region SR as shown in FIG. 2A.

Figure 2B:
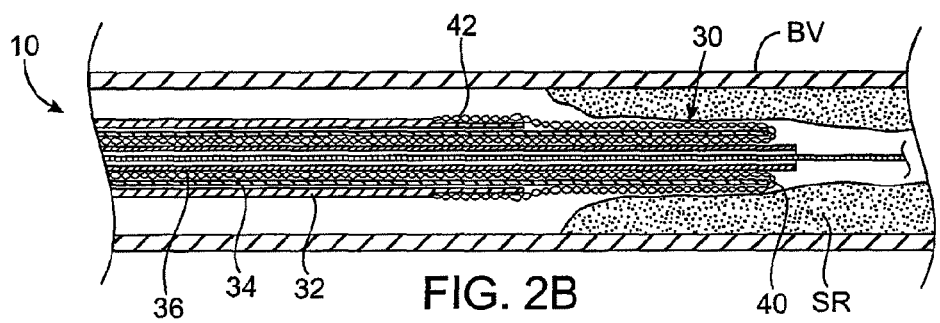

At that point, the prosthesis 30 is advanced forwardly or distally into the stenosed region SR of the blood vessel BV, as shown in FIG. 2B. In particular, both the inner tube 36 and the middle tube 34 are advanced forwardly or distally relative to the outer tube 32. This causes the leading edge 40 of the prosthesis 30 to advance into the stenosed region SR, engaging and partially dilating the lumen wall within this region.

Figure 2C:
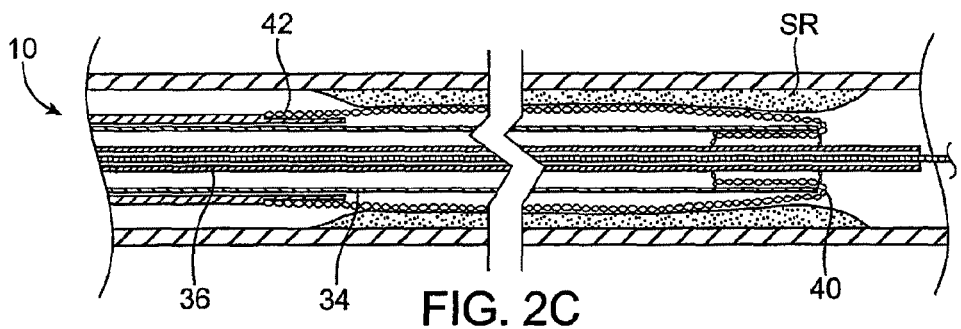

As the inner tube 36 and middle tube 34 are further advanced, as shown in FIG. 2C, the leading edge 40 of the prosthesis advances out through the other end of the stenosed region SR. During this entire deployment, fixed end 42 of the prosthesis has remained on the distal end of the outer tube 32 of the delivery catheter 10.

Figure 2D:
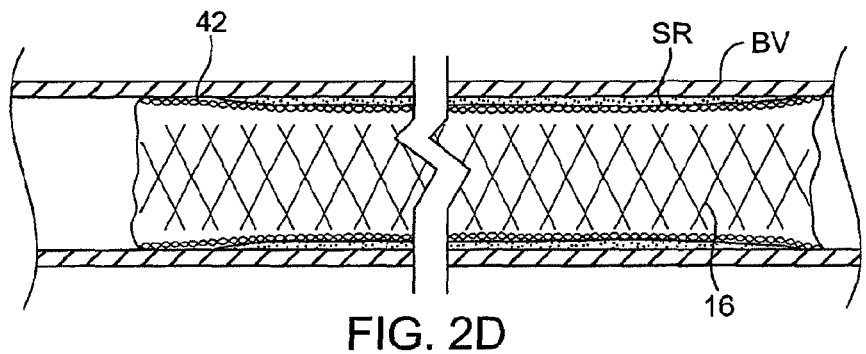

Once the prosthesis 30 is fully deployed, the outer tube 32 would be disengaged from the fixed end 42 of the prosthesis, e.g., by rotating or otherwise separating the catheter from the prosthesis, leaving the prosthesis 30 in place, as shown in FIG. 2D. As can be seen in FIG. 2D, the deployment of the prosthesis 30 has dilated the stenotic region. At this point, if the dilation is insufficient, or further anchoring of the prosthesis 30 is desired, a balloon or other expandable member may be expanded within the prosthesis 30 in a conventional manner. In one embodiment, for example, a balloon may be coupled with the outer tube 32 in such a way as to allow the balloon to be inflated to further anchor the prosthesis 30 in place.

It will be appreciated that the lengths, pitches, adjacent spacings, and the like, of the braided and other elements deployed according to the methods of the present invention can be controlled at the discretion of the treating physician. Thus, the methods and apparatus of the present invention provide useful flexibility for the treating physician to treat extended and disseminated disease in the vasculature and other body lumens.

Although the foregoing invention has been described in some detail by way of illustration and example, for purposes of clarity of understanding, it will be obvious that certain changes and modifications may be practices within the scope of the appended claims.

What is claimed is:

1. A method for delivering a prosthesis to a body lumen, said method comprising:
   positioning a delivery catheter at a target site, the tubular catheter comprising:
   an outer tube having a passage;
   a tubular prosthesis carried in the passage of the outer tube at least partially in a radially collapsed configuration; and
   an inner tube slidably disposed within the passage of the outer tube, the inner tube having a lumen for receiving a guidewire; and
   advancing the inner tube distally relative to the outer tube to evert the tubular prosthesis so that an inside surface is exposed radially outwardly and advanced over a length of a wall of the body lumen.

2. The method of claim 1, further comprising radially expanding the tubular prosthesis with an expandable member of the delivery catheter so that the tubular prosthesis applies a radially outward force against inner wall.

3. The method of claim 1, further comprising severing the tubular prosthesis with a separation element so that a first portion of the tubular prosthesis is deployed at the target site while another portion of the tubular prosthesis remains carried in the passage.

4. The method of claim 1, further comprising operating a handle at a proximal end of the delivery catheter to advance the inner tube to evert the tubular prosthesis.

5. The method of claim 1, further comprising inflating a balloon so as to anchor the tubular prosthesis to the body lumen.

6. The method of claim 1, wherein the delivery catheter further comprises a middle tube slidably disposed within the passage of the outer tube and slidably disposed over the inner tube, and wherein the method further comprises advancing the middle tube with the inner tube to evert the tubular prosthesis.

7. The method of claim 1, further comprising releasing a therapeutic agent from the tubular prosthesis after deployment thereof.

8. The method of claim 7, wherein the therapeutic agent inhibits restenosis.

* * * * *